United States Patent [19]

Nagata et al.

[11] Patent Number: 4,916,934

[45] Date of Patent: Apr. 17, 1990

[54] OXYGEN SENSORS

[75] Inventors: Hiroshi Nagata, Seki; Atsushi Iino, Nagoya; Nobuhide Kato, Aichi; Hiroshi Ishikawa; Yasuhiko Hamada, both of Nagoya, all of Japan

[73] Assignee: NGK Insulators, Ltd., Japan

[21] Appl. No.: 283,847

[22] Filed: Dec. 13, 1988

[30] Foreign Application Priority Data

Dec. 25, 1987 [JP] Japan ............................. 62-327387

[51] Int. Cl.[4] ............................................. G01N 27/56
[52] U.S. Cl. .......................................... 73/23; 204/428
[58] Field of Search ..................... 73/23, 27; 338/34; 204/426, 428, 431, 1 T

[56] References Cited

U.S. PATENT DOCUMENTS

| 4,038,034 | 7/1977 | Nakajima et al. | 204/428 |
| 4,065,372 | 12/1977 | Hacker et al. | 204/428 |
| 4,111,778 | 9/1978 | Davis et al. | 204/428 |
| 4,401,967 | 8/1983 | Miwa et al. | 338/34 |
| 4,507,192 | 3/1985 | Ebizawa et al. | 204/428 |
| 4,597,850 | 7/1986 | Takahasi et al. | 73/28 |
| 4,624,770 | 11/1986 | Yamada et al. | 204/426 |

FOREIGN PATENT DOCUMENTS

| 2351815 | 4/1975 | Fed. Rep. of Germany. |
| 2707983 | 9/1977 | Fed. Rep. of Germany. |
| 3543083 | 7/1986 | Fed. Rep. of Germany. |
| 1469698 | 4/1977 | United Kingdom. |
| 1515496 | 6/1978 | United Kingdom. |

Primary Examiner—Hezron E. Williams
Attorney, Agent, or Firm—Arnold, White & Durkee

[57] ABSTRACT

An oxygen sensor is disclosed, which includes a planar sensor element and a metallic cover. The planar sensor element is provided with a detecting section at least at one of outer side surfaces thereof for detecting a gas to be measured. The detecting section is protected with the metallic cover. The metallic cover is provided with gas introduction openings for introducing the gas into the metallic cover. The gas introduction openings are arranged so as not to be opposed to the detecting section of the oxygen sensor element. Guide plates are provided at the gas introduction openings, respectively for swirling the gas inside the metallic cover in a given direction. The metallic cover is provided with a gas discharge opening at a bottom face thereof.

4 Claims, 4 Drawing Sheets

FIG_1a
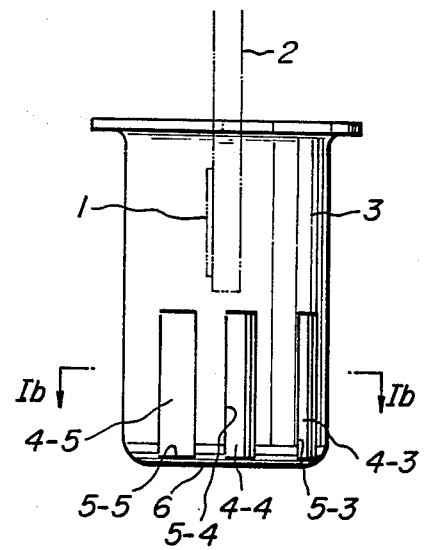
FIG_1b
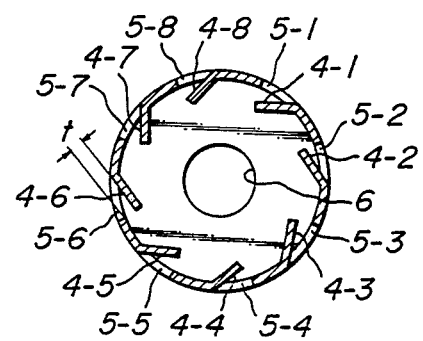

FIG_2a
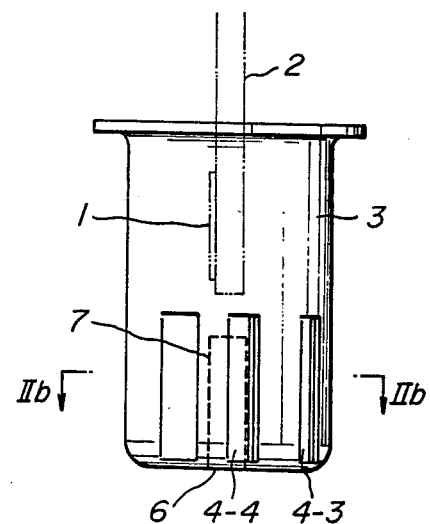
FIG_2b
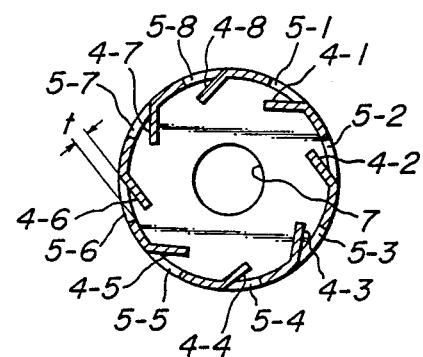

FIG_3
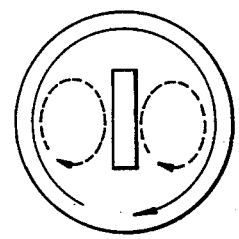
FIG_4a
FIG_4b
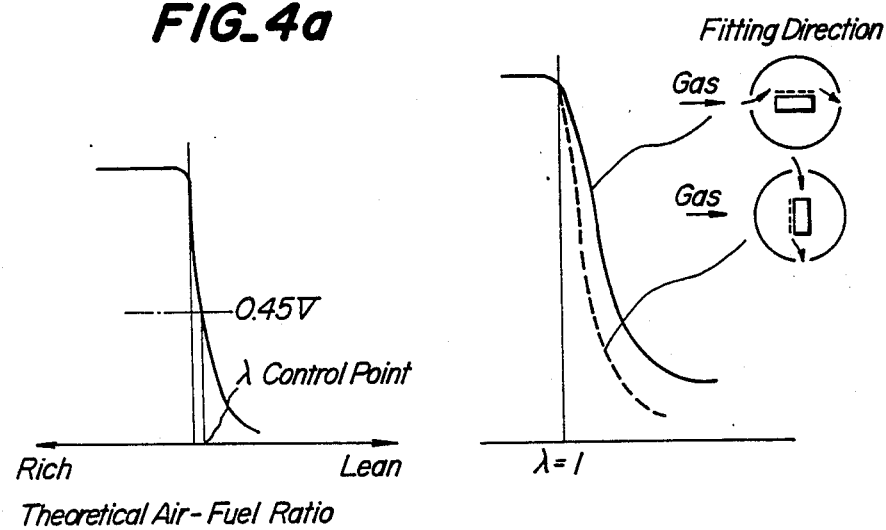

4,916,934

OXYGEN SENSORS

BACKGROUND OF THE INVENTION (1) Field of the Invention:

The present invention relates to oxygen sensors which can always provide optimum measurements without being influenced by a direction of contact of the measurement gas.

(2) Related Art Statement:

In order to improve the measuring accuracy of an oxygen sensor using a planar sensor element, Japanese Utility Model Registration Application Laid-open No. 60-150,447, NGK Insulators, Ltd. disclosed the oxygen sensor shown in FIG. 5a, in which a protection cover 22 protecting a planar sensor element 21 is provided with flow holes 23, through which a gas to be measured is introduced, which are not located at a position opposed to a wider surface of the sensor element. Reference numeral 25 denotes a gas discharge opening.

However, in the oxygen sensor described in Japanese Utility Model Registration Application Laid-open No. 60-150,447, a detecting section 24 is provided on the wider surface of the planar sensor element 21 as shown in FIG. 5b (a Vb—Vb sectional view of FIG. 5a). Therefore, the oxygen sensor has a shortcoming in that a direction in which the gas to be measured contacts the detecting section 24 depending upon the fitting direction thereof. The way in which the gas contacts the detecting section 24 differs between a case where the gas enters in an A-direction and a case where the gas enters in a B-direction. If the gas to be measured contacts the detecting section 24 in different directions like this, a λ control point of the sensor varies for reasons mentioned later. Consequently, high accuracy measurements cannot be obtained.

SUMMARY OF THE INVENTION

It is an object of the present invention to solve the above-mentioned problems, and to provide an oxygen sensor which uses a planar sensor element and whch can always effect measurement at high accuracy with a constant λ control point, regardless of a fitting direction of a detecting section.

According to the present invention, there is a provision of the oxygen sensor comprising a planar sensor element having, at least of one outer side surface thereof, a detecting section for detecting a gas to be measured, a metallic cover for protecting the detecting section of the sensor element, and gas introduction openings provided in the metallic cover for introducing the gas therein, characterized in that: the gas introduction openings are provided at a location of the metallic cover which is not opposed to the detecting section of the sensor element; guide plates are each provided at the gas introduction openings for swirling the gas inside the metallic cover in a given direction; and a gas discharge outlet is provided at a bottom face of the metallilc cover for discharging the gas to be measured.

In the above construction, the gas introduction openings are provided at the end portion of the metallic cover at a location not opposed to the detecting section of the sensor element so that the gas to be measured may not directly contact the detecting section, the guide plates are each provided at the respective gas introduction openings, and the gas discharge outlet is provided at the bottom of the metallic cover. Thereby, the gas is swirled inside the metallic cover in a given direction. Thus, even if the fitting location of the detecting section to the sensor element varies, the gas always contacts the detecting section in a constant state.

That is, as shown in FIG. 3, a uniform flow is produced by the guide plates, and spreads toward the planar sensor element. The swirl indicated by a solid line is then produced along the inner peripheral wall of the metallic cover at the detecting zone. Consequently, weak swirls are formed between the sensor element and the uniform swirl. Therefore, such swirls can always uniformly be formed regardless of the fitting direction of the oxygen sensor to the stream of the gas to be measured.

Since the gas discharge outlet is provided at the bottom of the metallic cover for discharging the gas to measured, the main flow of the gas peels off at the bottom. Consequently, the pressure lowers at the bottom face, and the gas inside the metallic cover is discharged to cause downward flow of the gas inside the metallic cover near the central portion. The downstream flow near the central portion of the metallic cover promotes the swirling and further uniformalize the flow. In addition, since the amount of the gas introduced to be measured increases by the amount of the gas discharged, the swirl is strengthened to further uniformalize the flow. Moreover, when a discharge pipe is added to the bottom face of the metallic cover, interference between the downward flow and the swirl inside the metallic cover is prevented so that the swirl can be further strengthened.

It is preferable to set the width of a gap "t" (see FIGS. 1b and 2b) between the guide plate and the remote side edge of the gas introduction opening, that is, an opening degree of the gas introduction opening, at not more than 0.8 mm and to provide not less than 6 guide plates, because the swirl can be further uniformalized in that case.

These and other objects, features and advantages of the invention will be appreciated upon reading of the following description of the invention when taken in conjunction with the attached drawings, with the understanding that some modfications, variations and changes of the same could be made by the skilled person in the art to which the invention pertains without departing from the spirit of the invention or the scope of claims apppended hereto.

BRIEF DESCRIPTION OF THE ATTACHED DRAWINGS

For a better understanding of the invention, reference is made to the attached drawings, wherein:

FIGS. 1a and 1b are a plan view and a cross sectional view of an embodiment of the oxygen sensor according to the present invention, respectively;

FIGS. 2a and 2b are a plan view and a cross sectional view of another embodiment of the oxygen sensor according to the present invention;

FIG. 3 is a diagrammatical view of illustrating the flow of the gas in the oxygen sensor according to the present invention;

FIGS. 4a and 4b are diagrams explaining the reason why the λ control point varies depending upon the way in which the gas to be measured detects the detecting section.

DETAILED DESCRIPTION OF THE INVENTION

Figure 5A:
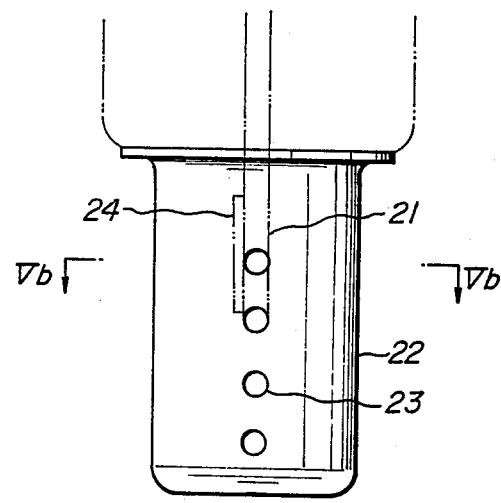
FIGS. 5a and 5b are a plan view and a cross sectional view of a conventional oxygen sensor.
Figure 5B:
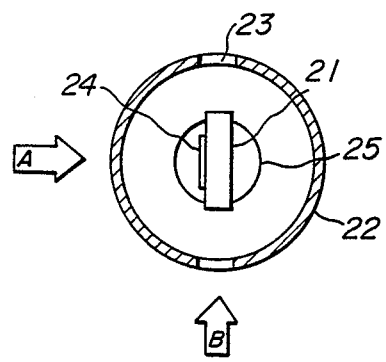

First, the reason why the $\lambda$ control point varies depending upon the direction and manner in which the gas to be measured contacts the detecting section will be explained below.

As shown in FIG. 4a, the $\lambda$ control point generally slightly shifts toward the lean side from the theoretical air-fuel ratio. The shifting is caused by the following phenomenon Even in the lean atmosphere (an oxygen-excess atmosphere), unburnt components such as CO and HC are present in a waste gas. The unburnt components are ideally converted to an equilibrated gas through reaction with excess oxygen. In this case, the $\lambda$ control point conforms with the theoretical air-fuel ratio. The above equilibrating reaction proceeds as the gas passes through a coating layer and a platinum layer of the oxygen sensor. If the reaction completely proceeds until the gas reaches the surface of a three-phase interface among the gas, the platinum, and zirconia as a substrate of the oxygen sensor element, the above ideal state is attained. However, in reality, this reaction does not completely proceed. Some of the unburnt components reach the three-phase interface, and react with $O^{--}$ in $ZrO_2$. Thus, for instance, $CO+O^{--}\rightarrow CO_2+2e$, so that electrons remain in the $ZrO_2$. That is, an electromotive force is generated at that part of the numerous three-phase interfaces where the unburnt components reach. Therefore, the electromotive force is generated even in the lean atmosphere, and accordingly the $\lambda$ control point apparently shifts toward the lean side. For this reason, when the gas to be measured strongly contacts the detecting section, an amount of the unburnt components reaching the surface of the three-phase interfaces increases so that the electromotive force becomes greater (the lean side shift becomes greater). When the gas weakly blows against the detecting section, the contrary results. Since the equilibrating reaction of the component becomes faster when the temperature rises, the lean side shift decreases with an increase in the temperature of the gas to be measured (the temperature of the sensor element). Therefore, how the waste gas contacts the detecting section and changes in the temperature of the sensor are factors causing deviations of the $\lambda$ control point. Consequently, as shown in FIG. 4b in the case of the conventional oxygen sensors, the $\lambda$ control point varies depending upon the fitting direction relative to the direction in which the gas to be measured flows.

FIGS. 1a and 1b are a plan view and a cross sectional view of an embodiment of the oxygen sensor according to the present invention, respectively. In the illustrated embodiment, a planar sensor element 2, which has, at its wider surface portion, a detecting section 1 conventionally constructed for detecting a gas to be measured, is fixed to an oxygen sensor body, which is not shown. The sensor element 2 is covered with a metallic cover 3. Eight gas introduction openings 5-1 through 5-8 are provided in the metallic cover 3 at locations not facing the detecting section 1 attached to the end of the sensor element 2, and eight guide plates 4-1 through 4-8 are provided behind the gas introduction opening 6 is provided in an end face of the metallic cover 3 for discharging outside the gas in the metallic cover 3. In this case, it is preferable that the "t" (see FIGS. 1b and 2b) of a gap between each of the guide plates 4-1 through 4-8 and a remote side edge of each of the respective gas introduction openings 5-1 through 5-8 is set at not more than 0.8 mm.

Regardless of the direction in which the detecting section 1 is fitted with respect to the flow of the gas to be measured, the gas to be measured will not directly contact the detecting section 1, and the gas flow inside the metallic cover 3 becomes a swirl rotating in a constant direction. Accordingly, as having been explained in connection with the function mentioned before, the flow of the gas is always kept constant wih respect to the detecting section 1.

Furthermore, each of the gas introduction holes is preferably formed by cutting corresponding guide plates in the metallic cover and inwardly erecting them.

FIGS. 2a and 2b are a perspective view and a cross sectional view of another embodiment of the oxygen sensor. In this embodiment, the same members or parts are denoted by the same reference numerals as in the first embodiment of FIGS. 1a and 1b, and their explanation is omitted. The embodiment in FIGS. 2a and 2b differ from that in FIGS. 1a and 1b in that a gas discharge pipe 7 is erected from the gas discharge opening of the metallic cover 3 by a given distance. In the illustrated embodiment, the interference between the flow toward the end portion of the metallic cover 3, that is, the downward flow and the swirl is prevented to strengthen the swirl.

As a matter of course, the present invention is never limited to the above-mentioned embodiments, but various modificatitons, variations and ehanges could be made. For instance, although the number of each of the gas inlet openings and the guide plates is both 8 in the above embodiments, the number is evidently not limited to 8. Further, it goes without saying that the shape of the guide plates is not limited to the one specifically illustrated.

As detailed above, according to the oxygen sensor of the present invention, the locations of the gas introduction openings and the structure of the guide plates are specified. Thereby, the gas to be measured can be prevented from directly contacting the detecting section, and the gas is swirled inside the metallic cover in a given direction. Therefore, even when the direction of the detecting section changes relative to the stream of the gas to be measured due to the direction of fitting the detecting section, the gas to be measured can contact the detecting section always in a constant state. Consequently, the constant $\lambda$ control point can be assured, and the measuring accuracy can be made constant.

What is claimed is:

1. An oxygen sensor comprising:
   a generally planar sensor element having a measurement gas detecting section provided at least on one outer side surface at an end portion thereof; and
   a metallic cover disposed around at least said detecting section, said metallic cover being of a single wall structure comprising:
   (a) a plurality of gas inlet openings for introducing the measurement gas into the metallic cover, said gas inlet openings being axially spaced from said detecting section in a longitudinal direction of said planar sensor element;
   (b) guide plates provided in each of said gas inlet openings for directionally swirling the measurement gas inside said metallic cover; and
   (c) a gas discharge opening located in a bottom surface of said metallic cover.

2. The oxygen sensor of claim 1, further comprising a gas discharge pipe fixed to the bottom surface of said metallic cover for discharging the measurement gas through said gas discharge opening.

3. The oxygen sensor of claim 1, wherein a gap defined between each of said guide plates and a remote side edge of each of said gas inlet openings is not more than 0.8 mm.

4. The oxygen sensor of claim 1, wherein at least six gas inlet openings are provided in said metallic cover.

* * * * *